US012636313B2

(12) United States Patent
Di Maio

(10) Patent No.: US 12,636,313 B2
(45) Date of Patent: May 26, 2026

(54) NUTRACEUTICAL OR PHARMACEUTICAL COMPOSITION COMPRISING IRON PYROPHOSPHATE FOR TREATING AND/OR PREVENTING IRON DEFICIENCY CONDITIONS OR DISEASES

(71) Applicant: NEILOS S.R.L., Piano di Sorrento (IT)

(72) Inventor: Umberto Di Maio, Sant'Agnello (IT)

(73) Assignee: NEILOS S.R.L., Piano di Sorrento (IT)

( * ) Notice: Subject to any disclaimer, the term of this patent is extended or adjusted under 35 U.S.C. 154(b) by 916 days.

(21) Appl. No.: 17/756,231

(22) PCT Filed: Nov. 19, 2020

(86) PCT No.: PCT/IB2020/060886
§ 371 (c)(1),
(2) Date: May 19, 2022

(87) PCT Pub. No.: WO2021/099976
PCT Pub. Date: May 27, 2021

(65) Prior Publication Data
US 2023/0000907 A1      Jan. 5, 2023

(30) Foreign Application Priority Data

Nov. 19, 2019    (IT) ........................ 102019000021564

(51) Int. Cl.
| | |
|---|---|
| *A61K 33/26* | (2006.01) |
| *A23L 33/00* | (2016.01) |
| *A23L 33/16* | (2016.01) |
| *A61K 9/00* | (2006.01) |
| *A61K 9/16* | (2006.01) |
| *A61K 31/718* | (2006.01) |

(52) U.S. Cl.
CPC .............. *A61K 33/26* (2013.01); *A23L 33/16* (2016.08); *A23L 33/30* (2016.08); *A61K 9/0056* (2013.01); *A61K 9/16* (2013.01); *A61K 31/718* (2013.01)

(58) Field of Classification Search
CPC ........ A61K 33/26; A61K 9/0056; A61K 9/16;

A61K 31/718; A61K 31/685; A61K 9/1652; A61K 9/1617; A23L 33/16; A23L 33/30; A23L 33/165; A23V 2002/00; A23V 2250/1592; A61P 3/02
See application file for complete search history.

(56) References Cited

U.S. PATENT DOCUMENTS

| | | |
|---|---|---|
| 2004/0069300 A1 | 4/2004 | Roversi |
| 2019/0105393 A1 | 4/2019 | Lacorte et al. |

FOREIGN PATENT DOCUMENTS

| | | |
|---|---|---|
| WO | 2019025922 A1 | 2/2019 |

OTHER PUBLICATIONS

International Search Report and Written Opinion for International Patent Application No. PCT/IB2020/060886, mailed Feb. 26, 2021, 11 pages.
Susana Gómez-Ramírez et al., Sucrosomial Iron: A New Generation Iron for Improving Oral Supplementation, Pharmaceuticals, Oct. 4, 2018, p. 97, vol. 11, No. 4, MDPI, Basel, CH.
Karrout et al., Characterisation of ethylcellulose: starch-based film coatings for colon targeting, Internet citation, URL: https://www. tandfonline.com/doi/full/10.1080/03639040902858868?scroll=top &needAccess=true, (retrieved on Nov. 22, 2018), Drug Development and Industrial Pharmacy, May 8, 2009, pp. 1190-1200, vol. 35, Issue 10, Informa Ltd., GB.

*Primary Examiner* — Jessica Worsham
(74) *Attorney, Agent, or Firm* — Daniel A. Blasiole; DeWitt LLP

(57) ABSTRACT

Provided herein is a composition of substances preferably obtained from natural sources, which is effective in preventing and/or treating iron deficiency conditions or diseases. The composition includes iron pyrophosphate, phosphatidylserine, phosphatidylcholine and starch, preferably acetylated pregelatinised starch. The formulation gives the composition gastro-resistance properties and high bioavailability of the active ingredient iron pyrophosphate. The composition is prepared in the form of a solid, semi-solid or liquid pharmaceutical dosage, preferably for oral administration.

1 Claim, 1 Drawing Sheet

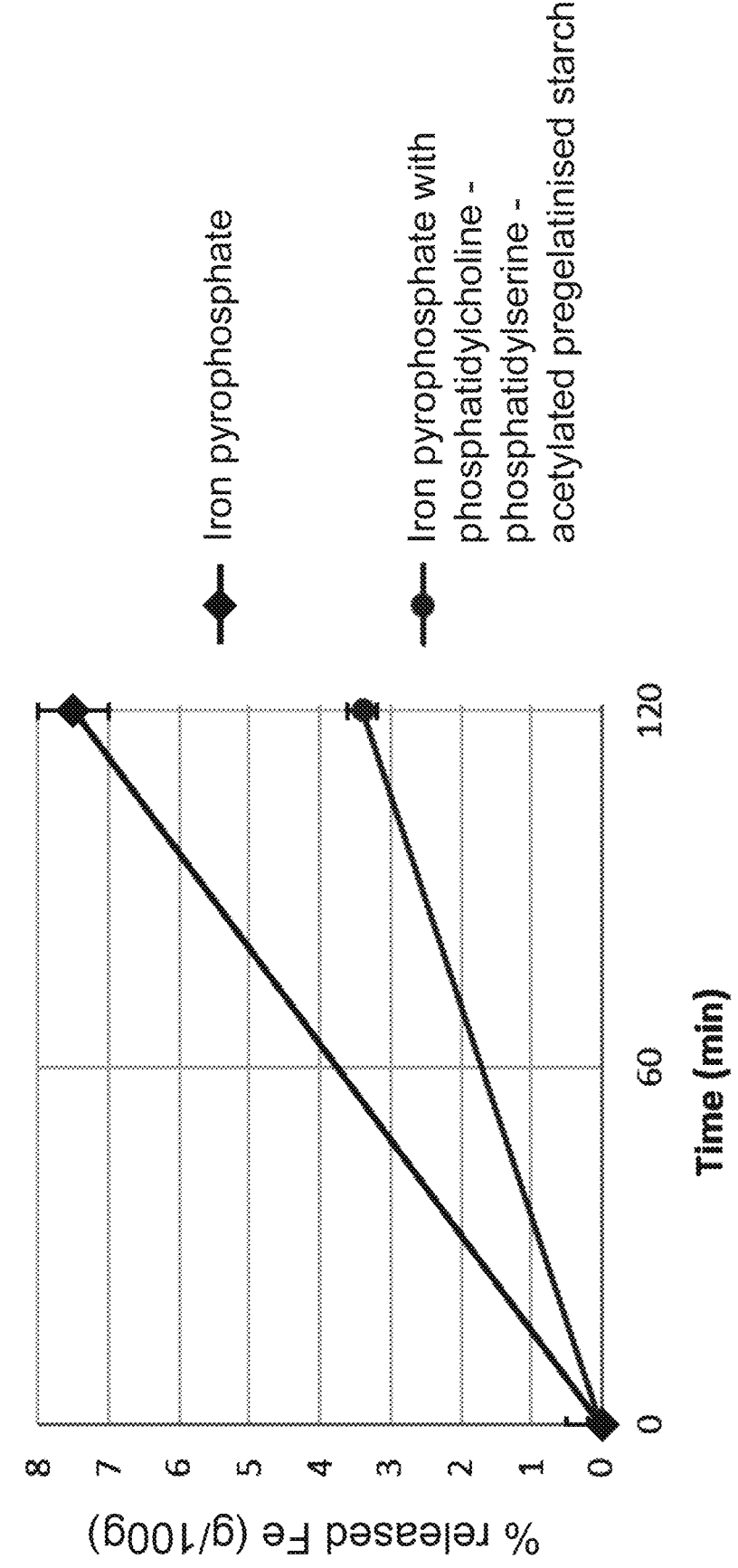

NUTRACEUTICAL OR PHARMACEUTICAL COMPOSITION COMPRISING IRON PYROPHOSPHATE FOR TREATING AND/OR PREVENTING IRON DEFICIENCY CONDITIONS OR DISEASES

CROSS-REFERENCE TO RELATED APPLICATIONS

This application is a National Stage Application of International Patent Application No. PCT/IB2020/060886, having an International Filing Date of Nov. 19, 2020 which claims priority to Italian Application No. 102019000021564, filed Nov. 19, 2019, the entire contents of which are hereby incorporated by reference herein.

FIELD OF THE INVENTION

The present invention relates to a nutraceutical or pharmaceutical composition of substances, which is effective in the prevention and/or treatment of conditions or diseases characterized by iron deficiency.

BACKGROUND OF THE INVENTION

Iron is an essential trace element that performs several vital functions in the human body and is involved in a plurality of metabolic processes: it transports oxygen through the bloodstream to the body parts, it is a cofactor in the synthesis of DNA, steroid hormones and bile acids, it carries electrons in the mitochondrial transport chain and detoxifies the body from foreign substances, as it is a part of the cytochrome p450. Iron is essential for a number of metabolic processes that occur at the cellular level; as it can also be potentially harmful, the biochemical effects and levels thereof are precisely controlled by sophisticated mechanisms which regulate its homeostasis at different levels. 70% of the body's iron is found in the blood bound to haemoglobin on red blood cells and is involved in the erythropoietic process. Haemoglobin is a globular protein formed by four polypeptide chains, each of which contains a haem group, consisting of a porphyrin ring surrounding and complexing an iron atom. Each iron atom can bind an oxygen molecule, thereby allowing oxygen to pass from the lungs to the bloodstream and be transported to all parts of the body. When red blood cells break down, iron is transported by transferrin into the bone marrow where it is reused for the production of new red blood cells. The remaining percentage of iron present in the body is linked to other tissue enzymes, to transport systems, such as transferrin, and to non-haem proteins, such as ferritin. The iron that can be absorbed by the human body through food is of two types: haem iron, which does not pose absorption problems, and non-haem iron, or inorganic iron, which instead exhibits very low bioavailability. Although it is the major source of iron in the diet, inorganic iron is absorbed only when it is in the reduced state ($Fe^{2+}$), which is the form favoured by the acidic pH of the stomach and the proximal duodenum. Whereas, at physiological pH, inorganic iron is rapidly oxidized to $Fe^{3+}$.

Although the amount of iron absorbed from the diet is very low, the human body is able to maintain normal levels of iron through continuous recycling of the deposits present in the cells and preventing the excretion thereof. The amount of iron eliminated by the body every day is very low ($\approx 1$ mg/day). The elimination of iron essentially takes place through exfoliation of the epithelial cells of the skin and the mucous membranes of the genitourinary and gastrointestinal tracts. However, there are certain categories of individuals who are more prone to develop more or less moderate forms of iron deficiency, basically due to inadequate intake of iron with the diet under conditions of increased need for it. The subjects at risk include:

Children and adolescents: iron is essential for proper body growth, therefore growth in the absence of adequate supplementation thereof is one of the main factors that could cause deficiency;

Women of reproductive age: the loss of blood during menstruation increases, almost doubling, the need for iron that a woman of childbearing age should take with her diet;

Pregnant women: there is a significant increase in iron requirements during pregnancy due to the rapid growth of the placenta and the fetus;

Subjects with reduced intestinal absorption: this category includes anyone suffering from diseases characterized by malabsorption such as chronic inflammatory bowel disease, coeliac disease or obesity. The latter is a condition accompanied by a state of chronic inflammation and high levels of hepcidin, a peptide hormone that inhibits ferroportin1 on the enterocyte basolateral membrane and macrophage ferroportin, inhibiting both intestinal absorption and macrophage release of the iron already present in the body.

Iron deficiency can occur with or without anaemia, but most of the iron deficiency symptoms are essentially attributable to the anaemia picture. The term "anaemia" refers to a condition characterized by changes in the number of red blood cells or haemoglobin in the blood, which falls to a level lower than that required for the correct transport of oxygen to all body areas and tissues. The anaemia caused by a lack of iron is defined as "iron deficiency anaemia" and can occur in subjects who are unable to reach adequate levels of this essential element through the diet, or in subjects suffering from morbid conditions characterized by chronic blood loss (such as gastric ulcers, colon or uterine cancer, intestinal polyps and haemorrhoids), in pregnant women and in obese individuals. The main typical symptoms of iron deficiency anaemia include: a sense of fatigue, weakness and reduced resistance; difficulty concentrating and reduced physical and mental performance; pallor; shortness of breath; difficulty maintaining adequate body temperature (in particular at the extremities that are cold); in pregnancy, it can lead to increased risk of preterm birth. In cases of more serious deficiencies, symptoms may appear as follows: glossitis (inflammation of the tongue which becomes red, swollen and painful); chapped lips; neurological symptoms such as pica (need to eat substances such as dirt, ice and paint).

As mentioned above, the percentage of iron absorbed through food is very low, therefore, in certain conditions or stages of life, it is essential to resort to supplementation. This last strategy is not always easy to implement as inorganic iron exhibits a number of delivery problems. First of all, all iron salts have a characteristic smell and taste of rust that is extremely unpleasant, thus negatively affecting the compliance of any supplement containing inorganic iron. Another important problem related to its delivery is its modest absorption which, as mentioned, is affected by its redox state. The only form that can be absorbed in the intestine is the reduced form ($Fe^{2+}$). The reduced state is favoured by the acidic pH values found in the stomach and the proximal duodenum. Therefore, intestinal absorption of inorganic iron is limited to this tract, since the pancreatic juice in the remaining portion of the intestine instead favours the oxidised state ($Fe^{3+}$). Some iron salts, such as pyrophosphate, exhibit poor suspendability and a high tendency to sediment. This feature causes iron, when in contact with the gastric mucosa, on the one hand to be oxidised due to the contact with the basic mucus, and on the other to irritate the mucous membrane. Furthermore, in most patients, oral administration of iron causes undesirable gastrointestinal effects, such as abdominal pain, diarrhoea or constipation, nausea and vomiting.

SUMMARY OF THE INVENTION

Therefore, the object of the present invention is to provide a nutraceutical or pharmaceutical composition suitable for delivering iron, so as to replenish its levels in subjects who are deficient in this element.

Iron pyrophosphate is one of the most commonly used salts in iron supplements. Pyrophosphate is a substance that takes part in the energy cycle and is produced by the hydrolysis of adenosine triphosphate. When combined with multivalent cations, it is capable of forming water-insoluble complexes featuring considerable chemical and structural complexity. This feature makes pyrophosphate one of the most commonly used compounds in the chemical and biomedical industries.

The most suitable inorganic salt is selected by taking into consideration several factors, the first of which is effectiveness. Many clinical studies have shown that iron pyrophosphate is among the salts that provide the best results, even in the most severe cases of iron deficiency. Among cancer patients, iron deficiency is one of the most common nutritional deficiencies and can be a secondary effect caused by increased erythropoiesis, decreased intestinal absorption capacity, increased blood loss or chronic bleeding, increased exfoliation of gastrointestinal epithelial cells. A clinical study performed on 42 subjects with advanced cancer and plasma iron levels below 60 μg/dL investigated the effects of a 30-day treatment with iron pyrophosphate on hyposideraemia. The results obtained showed that a dose of 30 mg/day of iron pyrophosphate enhanced the sideraemia, ferritinaemia and haemoglobinaemia levels, without appearance of side effects.

Another factor to be taken into consideration is the change in the organoleptic characteristics. The majority of the water-soluble inorganic iron (II) salts, such as iron sulphate, in fact cause unpleasant changes in the taste and colour of the supplements in which they are inserted. Iron pyrophosphate, on the other hand, is extremely advantageous as it does not change the colour of the supplements in which it is inserted. However, iron (III) salts, such as iron pyrophosphate, have the disadvantage of being less water-soluble and less bioavailable than iron (II) salts. The lower bioavailability of iron (III) salts is related with their moderate solubility in diluted acids, such as those found in gastric juices.

Therefore, there is a need to provide a nutraceutical or pharmaceutical composition containing iron pyrophosphate as the active ingredient, which overcomes the drawbacks and disadvantages of the prior art, in particular which features high iron bioavailability.

There is also a need to provide a nutraceutical or pharmaceutical composition containing iron pyrophosphate as the active ingredient, which is endowed with gastro-resistant characteristics.

These and other needs are met by the present invention which, in a first aspect, provides a nutraceutical or pharmaceutical composition characterised in that it comprises iron pyrophosphate as the active ingredient and a combination of three functional excipients, preferably from natural sources, i.e. phosphatidylserine, phosphatidylcholine and starch, which are capable of providing gastro-resistant properties and increasing iron bioavailability. The nutraceutical or pharmaceutical composition of the invention is particularly effective in the treatment and prevention of conditions and diseases, including related symptoms, caused by iron deficiency. Iron deficiency may be due to reduced dietary intake or increased requirements.

A pharmaceutical product or a food supplement comprising the nutraceutical or pharmaceutical composition according to the invention also fall within the scope of the invention. In addition to the active ingredient iron pyrophosphate and the functional excipients starch, phosphatidylcholine and phosphatidylserine, the pharmaceutical product or food supplement of the invention can optionally comprise further active ingredients and functional excipients, which can be readily selected by those skilled in the art based on the relevant requirements. The selection of carriers, excipients and/or diluents required for the formulation of the pharmaceutical product or food supplement into an appropriate dosage form also falls within the average skills of the person skilled in the art.

BRIEF DESCRIPTION OF THE FIGURE

The FIGURE shows iron release into a sham gastric environment where iron values are expressed as grams per 100 grams of formulation (g/100 g).

DETAILED DESCRIPTION

A detailed description of some preferred embodiments of the invention is provided hereinafter.

As indicated, the nutraceutical or pharmaceutical composition of the present invention comprises iron pyrophosphate as the active ingredient and a combination of functional excipients which provide the composition with gastro-resistant properties and increased iron bioavailability. Such a combination of functional excipients includes phosphatidylcholine, phosphatidylserine and starch.

The nutraceutical or pharmaceutical composition of the invention is therefore particularly effective for the delivery and supplementation of iron for counteracting the typical symptoms of iron deficiency states and for providing high levels of this element in periods of reduced dietary intake or increased iron requirements. Examples of these conditions and diseases are anaemia, iron deficiency, pregnancy and breastfeeding, loss of appetite, asthenia, menstruation, bleeding and menopause, inflammatory bowel disease, coeliac disease, obesity, gastric ulcers, colon or uterine cancer, intestinal polyps, haemorrhoids.

Starch is a polysaccharide organic compound consisting of repeating glucose units linked by α-glycosidic bonds. It consists of two types of polymers: amylose, which generally accounts for approximately 20%, and amylopectin, which generally accounts for approximately 80%. Amylose is the central part of the starch granules, is soluble in very hot water and consists of glucose molecules linked by α-1,4 glycosidic bonds. Amylopectin is a highly branched polymer forming the outer part of the granules. The monomeric units composing it are linked, at the branching points, by α-1,6 glycosidic bonds. In nature, it forms in the green parts of plants, and is then accumulated in the storage organs, such as tubers, seeds and roots. Due to its properties and characteristics, it has always found many industrial uses.

Starch is of particular importance in the food industry, which uses it as a thickening agent and in the production of sweeteners such as maltitol and sorbitol. Thanks to its adhesive properties, it is also used in the production of paper and glues, in the form of starch water. In the pharmaceutical industry, starch has always been used as an excipient and for the formation of coatings, thanks to its binding properties.

Although starch is also used in its natural form, the interest of companies is mainly aimed at modified starches, that is, starch molecules suitably modified to meet the needs of the various production processes in which starch is used. These modified starches can be obtained by using as the source plants that have undergone natural or induced genetic mutations and which therefore produce starches with altered characteristics. Another strategy is to modify starch, generally from corn, tapioca and rice, through chemical (addition of functional groups, treatment with acids and bases), physical (gelatinization) or enzymatic (partial hydrolysis) treatments. Dextrins are exemplary modified starches obtained by hydrolysis and re-polymerization. These reactions can be carried out either by simple thermal degradation or by acid catalysis. As a consequence, molecules characterized by shorter chains which are therefore partially or totally water-soluble are obtained. Examples of dextrins are cyclodextrins and maltodextrins, which are excipients widely used in the nutraceutical and pharmaceutical fields.

The nutraceutical and pharmaceutical industries have shown great interest in modified starches with high amylose content (HAS, High Amylose Starch). A starch, to be defined as such, must have an amylose percentage of at least 50%. High amylose starch can be obtained from genetically modified plants or by adding amylose to low amylose starches. Strategies employed by various companies include the use of HAS for the preparation of solid pharmaceutical forms or in coating processes. HAS has several advantages over other types of starches, such as better consistency, greater thermal stability and greater resistance to humidity and adhesion phenomena. Several strategies have been put in place to make the most of the advantages of HAS. Scherer Corporation, for example, is credited with using soft gel capsules in which a certain percentage of gelatin is replaced with the aforementioned starch. The capsules thus obtained have better appearance and greater resistance. Dow Chemical Company can boast the use of capsules which are more uniform and exhibit greater stability in water and at high temperatures thanks to the use of hydroxyalkylated HAS. Upjohn Company boasts the use of amylose acetate phthalate as a coating agent in gastro-resistant preparations.

Various types of starch can be used in the present invention. By way of example, the following are mentioned: a non-chemically modified pregelatinised corn starch, or an acetylated pregelatinised corn starch with high amylose content which, in this specific case, can reach up to 90% by weight. The percentage of acetyl groups is between 0.5% and 2.5%, including all intermediate values, i.e. 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3% and 2.4%. Acetylated pregelatinised starch is the most preferred form of starch.

Acetylation is carried out with acetic anhydride which guarantees that a percentage of acetyl groups higher than 0.5%, but not higher than 2.5%, shall be reached. Pregelatinization treatment of starch consists in dispersing acetylated starch in water and subjecting the resulting dispersion to temperatures between 100 and 130 degrees and high pressures. Starch granules subjected to this procedure burst and form a gel with a moisture content of between 5 and 10%. Once solidified and removed, the modified starch thus obtained can be used in processes for coating hard and soft capsules and microgranules and guarantees that the resulting coating will be at the same time resistant and adequately viscous, capable of masking unpleasant odours and tastes, and also usable in case a gastro-resistant or modified release pharmaceutical form is desired. The features of the pharmaceutical form can be tuned by changing the amount of starch used in the coating.

Tests carried out by using the aforementioned starch showed its gastro-resistant action, its protection against moisture and its ability to release the active ingredient into the intestinal environment within minutes.

As indicated, further functional excipients occurring in the nutraceutical or pharmaceutical composition of the invention are phosphatidylcholine and phosphatidylserine. These compounds belong to the large class of phospholipids. Phospholipids are molecules structurally very similar to triglycerides. They consist of a glycerol molecule esterified at position 1 and 2 with fatty acids. Fatty acids occurring in the composition of natural phospholipids can have a length ranging from 12 to 22 carbon atoms; position 1 generally bears a saturated fatty acid, position 2 bears unsaturated fatty acids; position 3 bears a phosphate group which, in turn, is esterified with a complex molecule of various kinds, such as choline, serine, ethanolamine or inositol. These molecules are the ones after which the phospholipid is named (phosphatidylcholine, phosphatidylserine, phosphatidylethanolamine and phosphatidylinositol) and which affect its physical properties as they determine whether the molecule is anionic (such as phosphatidylserine) or zwitterionic (such as phosphatidylcholine). The peculiar chemical structure makes phospholipids amphiphilic molecules, i.e. molecules capable of interacting with both polar and non-polar solvents. More precisely, the carbon chains of the fatty acids represent the non-polar portion that interacts with non-polar solvents, whereas the phospholipid head, consisting of the phosphate group and the molecule linked to it, represents the polar part that interacts with water and other polar solvents. This structural feature makes them molecules with surfactant properties which, above a certain temperature defined as the critical micelle concentration, aggregate forming characteristic complexes that can vary in shape and size according to the conditions of the environment in which they are formed and to the chain length of the fatty acids that compose them. For example, if dispersed in an aqueous solution, they form micelles having a typical shape, with their polar heads facing outwards towards the aqueous environment and their hydrophobic tails facing inwards. On the other hand, if dispersed in organic solvents, they form the so-called reverse micelles, in which the heads face inwards and the tails the external non-polar environment. As for the size, they vary according to the length of the carbon chains of the fatty acids that make up the phospholipids.

Phospholipids are highly significant molecules from a biological point of view, firstly because they take part in making up biological membranes, and secondly because they are involved in several complex mechanisms such as the transduction of intracellular signals, the regulation of the intracellular concentration of some ions, and the mediation of inflammatory processes as they are sources of arachidonic acid. Phospholipids are interesting molecules also from a technological point of view and therefore are used in the pharmaceutical and nutraceutical fields as technological adjuvants in the formulation of delivery systems for various active ingredients. Many active ingredients may in fact have poor bioavailability caused by the difficulty in crossing the biological barriers and membranes of many parts of the body. Phospholipids, and in particular phosphatidylcholine and phosphatidylserine, are a valuable aid in the field of technological strategies for releasing various active ingredients. One of the advantages of phospholipid-based delivery systems is the compatibility of phospholipids with cell membranes, both at the mucosal level and at the skin level. Therefore, phosphatidylcholine and phosphatidylserine act as intestinal and topical absorption enhancers and this action can be attributed to the following mechanisms of action:

thanks to their properties and structure, they can fuse with the stratum corneum and membrane lipids and disrupt their structure, thereby allowing the passage of various substances;

when in contact with intestinal fluids they form micelles which help increase the absorption of the active ingredients of interest as they extract lipids from membranes and change the rheological properties, fluidity and composition of the membranes, increasing the permeability thereof;

the aforementioned micelles protect the active ingredients from chemical and enzymatic degradation and can be absorbed into the enterohepatic circulation of bile salts, together with the mixed micelles of the diet, and be transported into the bloodstream where they release the incorporated active ingredients.

Therefore, the present invention can provide:

Gastro-resistance

Increased iron bioavailability

The present invention represents a ready and effective intervention for counteracting the typical symptoms of iron deficiency states and for providing adequate levels of this element in periods of reduced dietary intake or increased requirements. This effect is ascribed to the combined action of the substances that compose it. The starch used in the present invention allows for the masking of the unpleasant taste that can be found in iron-based supplements, as well as for the protection of iron from the acidic pH of the stomach, ensuring its release in the intestine. Phosphatidylcholine and phosphatidylserine increase iron bioavailability thanks to the multi-mechanism action at the intestinal mucosa.

The effectiveness of the nutraceutical or pharmaceutical composition object of the present invention is assessed by means of the experimental protocol described hereafter.

In order to assess gastro-resistance, a disruption test was performed, as prescribed by the Pharmacopoeia. A sample of the pharmaceutical form to be tested was placed in a special implement containing 0.1 N hydrochloric acid. The gastro-resistant pharmaceutical form, in contact with the buffer at pH 2 for two hours, does not undergo disruption. The sample was then transferred to a pH 6.8 buffer where it underwent disruption within ten minutes.

Gastro-resistance can also be assessed by a Pharmacopoeia dissolution test wherein the pharmaceutical form is contacted with a 0.1 N hydrochloric acid solution; to pass the test, it must release less than 20% iron in 2 hours.

An in vitro test on human-derived Caco-2 cells is performed to assess intestinal permeability. Cultured cells are prepared by using a suitable growth medium (for example containing FBS, fetal bovine serum) and maintained under controlled conditions (for example at 37° C., in a 5% $CO_2$ and 100% humidity atmosphere). After several steps the cells are washed and pre-incubated with PBS. Following the treatment with the formulations of interest, the collected samples are analysed to quantify the iron.

A variation of the aforementioned in vitro test, discussed by way of example, provides that the Caco-2 cells are incubated under the same conditions of temperature, $CO_2$ and humidity. After the medium is aspirated, the cells are washed twice with a suitable buffer (for example 50 mM HEPES, 130 mM NaCl, 10 mM KCl, 5 mM glucose, 1 mM $MgSO_4$, pH 7) and then treated with the samples to be tested for one hour. At the end of the treatment, the cell monolayer is washed with a buffer that removes the iron and dissolved in a suitable medium (for example 2% Triton-X) for sonication. Protein concentration is calculated by using a special method (for example, the bicinchoninic acid assay). Iron concentration is obtained by atomic absorption and the uptake is expressed as μg of iron per mg of protein.

Another variation provides that the Caco-2 cells are sown in transwells and allowed to grow for at least 21 days. After this period that is necessary for the formation of a differentiated and polarized monolayer, the TEER (transepithelial electrical resistance)—a parameter that provides information on the integrity of epithelial tight junctions and cell monolayers grown on semi-permeable supports—is measured. Only transwells with a certain value (for example TEER>200 Ω·cm2) are taken into consideration.

The solution containing the composition object of the present invention is subjected to gastric and intestinal digestion and is then applied (at the concentrations selected on the basis of the results of the preliminary cytotoxicity) to the apical side of the transwell (which in the model represents the intestinal lumen). At predetermined time intervals (for example after 1-2-3-4 hours), liquid is collected from the basolateral side and subsequently analysed for the amount of iron pyrophosphate by ICP or other accredited method.

Iron uptake can again be assessed in the Caco-2 cell model by assessing the ferritin in the cell after treatment with the samples. The percentage of ferritin is directly proportional to the amount of iron inside the cell.

The effectiveness of the present invention can also be assessed by an in vivo test on experimental animals in accordance with the directives of the European Community and the Ministry of Health and approved by an Ethics Committee. The test is carried out on male, for example Sprague-Dawley mice weighing on average about 250-300 g. In the first part of the study, the iron level is assessed after a single administration of the formulation under examination. Plasma iron levels are measured by atomic absorption or other suitable analytical technique in blood samples taken at time zero and at predetermined time intervals after administration. The second part of the study assesses the plasma iron levels after daily administration of the above formulation for a prolonged period of time and, at the end of the treatment, the blood levels of iron, haemoglobin, transferrin and ferritin.

The effectiveness of the composition object of the present invention can also be assessed through a clinical trial in humans by monitoring, after a predetermined period of time, the change in the blood levels of iron, haemoglobin, transferrin and ferritin, before and after administration of the formulation object of the present invention.

The nutraceutical or pharmaceutical composition of the present invention is particularly effective in counteracting iron deficiency states thanks to the synergistic action of its components.

As indicated above, the nutraceutical or pharmaceutical composition of the present invention is inserted in a pharmaceutical product or food supplement, which is formulated into a suitable dosage form, the making and preparation of which falls within the skills of the person skilled in the art.

In a preferred embodiment, the iron pyrophosphate in the nutraceutical or pharmaceutical composition of the invention is present in an amount of between 0.1 and 90%, preferably between 1 and 80%, even more preferably between 5 and 70% of the total weight of the composition.

By way of example, further percentages of iron pyrophosphate that can be used in the composition of the invention are: 2%, 3%, 4%, 6%, 7%, 8%, 9%, 10%, 15%, 20%, 25%, 30%, 35%, 40%, 45%, 50%, 55%, 60%, 65%, 75%, or 85%.

In another preferred embodiment, the starch in the nutraceutical or pharmaceutical composition of the invention is present in an amount of between 0.1 and 90%, preferably between 1 and 80%, even more preferably between 10 and 70% of the total weight of the composition.

By way of example, further percentages of starch that can be used in the composition of the invention are: 2%, 3%, 4%, 6%, 7%, 8%, 9%, 10%, 15%, 20%, 25%, 30%, 35%, 40%, 45%, 50%, 55%, 60%, 65%, 75%, or 85%.

In yet another preferred embodiment, the phosphatidylcholine in the nutraceutical or pharmaceutical composition of the invention is present in an amount of between 0.01 and 50%, preferably between 0.05 and 30%, even more preferably between 0.1 and 10% of the total weight of the composition.

By way of example, further percentages of phosphatidylcholine that can be used in the composition of the invention are: 0.02%, 0.03%, 0.04%, 0.06%, 0.07%, 0.08%, 0.09%, 0.2%, 0.3%, 0.4%, 0.6%, 0.7%, 0.8%, 0.9%, 1%, 2%, 3%, 4%, 5%, 6%, 7%, 8%, 9%, 15%, 20%, 25%, 35%, 40%, or 45%.

In still another preferred embodiment, the phosphatidylserine in the nutraceutical or pharmaceutical composition of the invention is present in an amount of between 0.05 and 30%, even more preferably between 0.1 and 10% of the total weight of the composition.

By way of example, further percentages of phosphatidylserine that can be used in the composition of the invention are: 0.02%, 0.03%, 0.04%, 0.06%, 0.07%, 0.08%, 0.09%, 0.2%, 0.3%, 0.4%, 0.6%, 0.7%, 0.8%, 0.9%, 1%, 2%, 3%, 4%, 5%, 6%, 7%, 8%, 9%, 15%, 20%, 25%, 35%, 40%, or 45%.

All of the above preferred embodiments can be combined with each other.

The pharmaceutical product or food supplement, which comprises the pharmaceutical or nutraceutical composition of the invention, is formulated into a preferably oral pharmaceutical form, which can be solid, semi-solid or liquid.

By way of example, a powder, a mouth-soluble powder, a granulate, a hard capsule, a soft-gel capsule, a tablet, a sachet, a solution, a suspension or an emulsion are mentioned.

Some non-limiting examples of nutraceutical or pharmaceutical compositions object of the present invention are given below. As indicated above, these nutraceutical or pharmaceutical compositions are formulated as pharmaceutical products or food supplements and administered in a suitable oral dosage form, optionally divided into one or more dosage units, such as, for example, a capsule, a tablet or a sachet.

The following examples are provided for illustration purposes only and are not intended to limit the scope of the invention as defined in the appended claims.

EXAMPLES

Example 1

| Active ingredient | Quantity % |
|---|---|
| Iron pyrophosphate | 54 |
| Acetylated MODIFIED STARCH AMPRAC01 44.2 | 44.2 |
| 30% Phosphatidylcholine | 1.2 |
| 60% Phosphatidylserine | 0.6 |

Example 2

| Active ingredient | Quantity % |
|---|---|
| Iron pyrophosphate | 54 |
| PREGELATINISED CORN STARCH VN 44.2 | 44.2 |
| 30% Phosphatidylcholine | 1.2 |
| 60% Phosphatidylserine | 0.6 |

Example 3

| Active ingredient | Quantity % |
|---|---|
| Iron pyrophosphate | 40 |
| PREGELATINISED CORN STARCH VN 44.2 | 55 |
| 30% Phosphatidylcholine | 3.6 |
| 60% Phosphatidylserine | 1.4 |

Example 4

| Active ingredient | Quantity % |
|---|---|
| Iron pyrophosphate | 60 |
| Acetylated MODIFIED STARCH AMPRAC01 44.2 | 35 |
| 30% Phosphatidylcholine | 2.5 |
| 60% Phosphatidylserine | 2.5 |

Example 5

The fluidized bed granulation technology was used for the preparation of the product "Granular iron pyrophosphate" An example of a preparation applied to the compositions of Examples 1 and 2 is given below. The manufacturing process consists of the following steps:

a) Mixing:

The raw materials previously loaded into the basket granulator are subjected to a first fluidized bed mixing step, with the working air having a temperature of 80-90° C., until a mixture having an average temperature of 44° C. is obtained. During this step, a bulk is created which is homogeneous as regards composition and temperature, an indispensable prerequisite for the optimal course of the subsequent granulation step.

b) Granulation

The granulation step comprises the insertion of an aqueous solution of a suitably chosen binding or granulation agent, by means of direct nebulization on the premixed and fluidized-bed bulk. In this step, the working air is again used at 90° C., appropriately selecting the speed of introduction of the binding solution in order to obtain a granulate which is structured according to the expectations (particle size, bulk density, flowability) and homogeneous.

c) Drying

During the drying step, the water content of the preformed granulate is basically brought back to the conditions of the starting mixture of raw materials. The temperature of the working air of the granulate at the end of the step is appropriately assessed in the pilot testing phase towards this objective.

d) Calibration

The semi-finished product obtained from the above step is transferred from the fluidized bed granulator to an oscillating granulator where it is calibrated through a sieve to reduce the particle size of the granules and agglomerates having a coarser structure.

Example 6

Iron Release into a Sham Gastric Environment 1 g of sample was weighed and introduced into the container of the dissolving apparatus containing 900 mL of 0.1 M HCl. The dissolution was performed for 2 h at 37° C. and 75 rpm. After dissolution, 1 mL of sample was diluted to 50 mL with 0.1 M HCl. The preparation was performed in six replicates for each sample.

The results thus obtained are shown in the FIGURE, where the iron values are expressed as grams per 100 grams of formulation (g/100 g).

The FIGURE shows that iron pyrophosphate as such (blue, upper line), not delivered with a functional excipient, after 120 minutes in the sham gastric environment, releases an amount of iron of 7.5 g±0.5 g per 100 g of formulation.

Iron pyrophosphate delivered with the combination of phosphatidylcholine, phosphatidylserine and acetylated pregelatinized starch (orange, lower line), after 120 minutes in the sham gastric environment, releases an amount of iron of 3.4 g±0.2 g per 100 g of formulation.

Therefore, the results thus obtained show that the composition according to the present invention, comprising iron pyrophosphate, phosphatidylcholine, phosphatidylserine and acetylated pregelatinized starch, is able to protect iron from the gastric environment in a much better way than what happens with iron pyrophosphate devoid of delivery systems. By minimizing the side effects due to premature release of iron into the stomach, the composition according to the present invention ensures that the almost total amount of iron will be available for absorption in the intestinal environment, thus promoting bioavailability, compliance and efficacy in all those conditions or diseases characterized by iron deficiency, such as anaemia, iron deficiency, pregnancy and breastfeeding, loss of appetite, asthenia, menstruation, bleeding and menopause, inflammatory bowel disease, coeliac disease, obesity, gastric ulcers, colon or uterine cancer, intestinal polyps, and haemorrhoids.

What is claimed is:

1. A method for improving absorption of iron in an intestinal environment in a subject in need thereof, the method comprising administering to the subject a nutraceutical or pharmaceutical composition comprising granulates consisting of a combination of iron pyrophosphate, phosphatidylcholine, phosphatidylserine, and acetylated pregelatinized starch, wherein the combination is a homogenous mixture.

* * * * *